(12) United States Patent
Hagen et al.

(10) Patent No.: US 7,998,205 B2
(45) Date of Patent: Aug. 16, 2011

(54) ARTIFICIAL MENISCUS PART AND KNEE-JOINT PROSTHESIS

(75) Inventors: Thomas Hagen, Tuttlingen (DE); Thomas Grupp, Denkingen (DE); Volkmar Jansson, Gilching (DE); Peter Mueller, Landsber am Lech (DE)

(73) Assignee: Aesculap AG, Tuttlingen (DE)

( * ) Notice: Subject to any disclaimer, the term of this patent is extended or adjusted under 35 U.S.C. 154(b) by 387 days.

(21) Appl. No.: 12/217,132

(22) Filed: Jun. 30, 2008

(65) Prior Publication Data

US 2009/0036984 A1  Feb. 5, 2009

(30) Foreign Application Priority Data

Jul. 4, 2007 (DE) .......................... 10 2007 032 150

(51) Int. Cl.
*A61F 2/08* (2006.01)
*A61F 2/38* (2006.01)
(52) U.S. Cl. ............... 623/14.12; 623/20.14; 623/20.15; 623/20.21; 623/20.3
(58) Field of Classification Search ............... 623/14.12, 623/18.11, 20.14–20.17, 20.21–20.33
See application file for complete search history.

(56) References Cited

U.S. PATENT DOCUMENTS

| 5,344,459 | A * | 9/1994 | Swartz | 623/14.12 |
|---|---|---|---|---|
| 5,871,539 | A * | 2/1999 | Pappas | 623/20.31 |
| 6,558,427 | B2 * | 5/2003 | Leclercq et al. | 623/20.33 |
| 6,893,463 | B2 * | 5/2005 | Fell et al. | 623/14.12 |
| 7,255,715 | B2 * | 8/2007 | Metzger | 623/20.17 |
| 2003/0093156 | A1 * | 5/2003 | Metzger et al. | 623/20.15 |
| 2003/0208278 | A1 * | 11/2003 | Richard | 623/20.14 |
| 2004/0064191 | A1 * | 4/2004 | Wasielewski | 623/20.14 |
| 2005/0021147 | A1 | 1/2005 | Tarabichi | |
| 2005/0278025 | A1 | 12/2005 | Ku et al. | |
| 2006/0111790 | A1 * | 5/2006 | Dietz | 623/20.32 |
| 2008/0091272 | A1 * | 4/2008 | Aram et al. | 623/20.34 |
| 2008/0161918 | A1 * | 7/2008 | Fankhauser et al. | 623/14.12 |
| 2008/0262624 | A1 * | 10/2008 | White et al. | 623/20.32 |
| 2009/0259314 | A1 * | 10/2009 | Linder-Ganz et al. | 623/14.12 |

FOREIGN PATENT DOCUMENTS

DE  198 19 180  3/2000

* cited by examiner

*Primary Examiner* — David Isabella
*Assistant Examiner* — Andrew Iwamaye
(74) *Attorney, Agent, or Firm* — Lipsitz & McAllister, LLC

(57) ABSTRACT

The invention relates to an artificial meniscus part for a knee-joint prosthesis that has on an upper side at least one femoral joint surface for the movable mounting of an artificial, natural or machined condyle of a femur, wherein the at least one femoral joint surface is configured in the form of a depression facing away from the meniscus part wherein the depression has an anterior and a posterior end region and a width of the depression has a minimum between the anterior and the posterior end region.

An improved meniscus part set, an improved knee-joint prosthesis and an improved knee-joint prosthesis set are further proposed.

34 Claims, 7 Drawing Sheets

ARTIFICIAL MENISCUS PART AND KNEE-JOINT PROSTHESIS

CROSS-REFERENCE TO RELATED APPLICATIONS

The present disclosure relates to the subject matter disclosed in German patent application number 10 2007 032 150.5 of Jul. 4, 2007 which is incorporated herein by reference in its entirety and for all purposes.

FIELD OF THE INVENTION

The present invention relates to an artificial meniscus part for a knee-joint prosthesis that has on an upper side at least one femoral joint surface for the movable mounting of an artificial, natural or machined condyle of a femur, wherein the at least one femoral joint surface is configured in the form of a depression facing away from the meniscus part.

The present invention further relates to a meniscus part set for a knee-joint prosthesis comprising a tibia part and at least one meniscus part, wherein the meniscus part is mounted immovably on the tibia part, wherein the meniscus part set comprises two or more differently shaped meniscus parts.

The present invention further relates to a knee-joint prosthesis having an artificial tibia part and having an artificial meniscus part, which is mountable movably or immovably on the tibia part and has on an upper side at least one femoral joint surface for the movable mounting of an artificial, natural or machined condyle of a femur, wherein the at least one femoral joint surface is configured in the form of a depression facing away from the meniscus part.

And finally the present invention relates to a knee-joint prosthesis set having at least one tibia part, at least one femur part and at least one meniscus part that is mountable between the at least one tibia part and the at least one femur part movably or immovably on the at least one tibia part.

BACKGROUND OF THE INVENTION

Meniscus parts and knee-joint prostheses of the initially described type are known in a large number of forms of construction and are implanted as a replacement for a completely or partially damaged knee joint. Artificial tibia parts are frequently partially flat or planar, so that the meniscus part inserted between femur or femur part and tibia part may transmit onto the tibia the load from the femur undergoing rolling/sliding motion. Depending on the shape of the meniscus part, the introduction into the meniscus part of the load exerted by the femur occurs in an areal, linear or even punctiform manner.

A problematical aspect of all known knee-joint prostheses is that in the event of incorrect implantation or a rotation of the tibia relative to the femur the contact surface between femur or femur part and meniscus part is reduced in size, thereby impairing an introduction of load from the femur onto the meniscus part because the surface pressure increases, this normally leading to excessive loading of the meniscus part and consequently to greater wear and possibly damage of the meniscus part.

An object of the present invention is, therefore, to improve a meniscus part, a meniscus part set, a knee-joint prosthesis and a knee-joint prosthesis set of the initially described type in such a way as to enable an introduction of load from the femur or a femur part onto the meniscus part over as large an area as possible even in the event of a rotation of femur and tibia relative to one another.

SUMMARY OF THE INVENTION

In a first aspect of the invention, an artificial meniscus part for a knee-joint prosthesis has on an upper side at least one femoral joint surface for the movable mounting of an artificial, natural or machined condyle of a femur. The at least one femoral joint surface is configured in the form of a depression facing away from the meniscus part. The depression has an anterior and a posterior end region and a width of the depression has a minimum between the anterior and the posterior end region.

In a second aspect of the invention, a meniscus part set for a knee-joint prosthesis comprises a tibia part and at least one meniscus part. The meniscus part is mounted immovably on the tibia part. The meniscus part set further comprises two or more differently shaped meniscus parts. At least one meniscus part of the set is a meniscus part as described above.

In a third aspect of the invention, a knee-joint prosthesis having an artificial tibia part and having an artificial meniscus part, which is mountable movably or immovably on the tibia part and at an upper side has at least one femoral joint surface for the movable mounting of an artificial or machine condyle of a femur. The at least one femoral joint surface is configured in the form of a depression facing away from the meniscus part. The depression has an anterior and a posterior end region and a width of the depression has a minimum between the anterior and the posterior end region.

In a fourth aspect of the invention, a knee-joint prosthesis set has at least one tibia part, at least one femur part and at least one meniscus part. The at least one meniscus part is mountable between the at least one tibia part and the at least one femur part movably or immovably on the at least one tibia part. The at least one meniscus part is a meniscus part as described above.

BRIEF DESCRIPTION OF THE DRAWINGS

The foregoing summary and the following description may be better understood in conjunction with the drawings figures, of which.

DETAILED DESCRIPTION OF PREFERRED EMBODIMENTS OF THE INVENTION

Although the invention is illustrated and described herein with reference to the specific embodiments, the invention is not intended to be limited to the details shown. Rather, various modifications may be made in the details within the scope and range of equivalents of the claims and without departing from the invention.

The present invention relates to an artificial meniscus part for a knee-joint prosthesis that has on an upper side at least one femoral joint surface for the movable mounting of an artificial, natural or machine condyle of a femur. The at least one femoral joint surface is configured in the form of a depression facing away from the meniscus part. The depression has an anterior and a posterior end region and the width of the depression has a maximum between the anterior and the posterior end region.

Equipping the meniscus part with a depression shaped in such a way has the advantage that in the region of the minimum of the width of the depression optimum guidance of the femur part by the meniscus part is made possible, yet by virtue of the increasing width of the depression in anterior and posterior direction the remaining femur or the femur part may nevertheless rest with a large area on the meniscus part, even when the tibia and the femur are rotated slightly relative to one another about their longitudinal axis, which may happen as a result of an incorrect implantation or a rotation owing to a relative movement of lower leg and thigh. Thus, wear of the proposed meniscus part is minimized compared to conventional meniscus parts. In particular, such a meniscus part is also suitable for being immovably mounted on a tibia part. This means that in such a situation a relative movement occurs exclusively between a machined natural femur part or an artificial femur part, in particular in each case a condyle thereof, and the meniscus part. The meniscus part according to the invention moreover not only makes it possible to produce a large contact surface between a femoral component and the meniscus part but also brings about a reduction of transverse forces acting upon the meniscus part, especially during femoral movements that do not extend precisely in anterior-posterior direction in relation to the meniscus part.

A shaping for the depression is made particularly easy if the depression, in a plan view, has a lobe-like or butterfly-like shape. The two described shapes are each so configured that a width of the depression has a minimum between the anterior and the posterior end region.

It may further be advantageous if the depression in plan view has a boundary line with the upper side that corresponds substantially to an external contour of a figure eight. The external contour of a figure eight also has a width that has a minimum between an anterior and a posterior end region of the meniscus part.

The meniscus part is particularly easy to manufacture if the depression is formed by at least two superimposed trough-like recesses, which each have a constant width between the anterior and the posterior end region, which define longitudinal axes in a plane parallel or substantially parallel to the upper side and which longitudinal axes form between them an acute angle of aperture oriented in anterior and/or posterior direction. Thus, for example, a first trough-like recess may be incorporated into the meniscus part by means of a tool and by rotating an orientation of the tool and of the meniscus part relative to one another about the angle of aperture a second trough-like recess may be introduced into the meniscus part. In this way, it is possible to machine the meniscus part using only one tool. It is naturally also possible to carry out a plurality of machining steps in the described manner, wherein relative orientations of machining tool and meniscus part differ in each case by a specific angle of aperture. It is of course also possible to manufacture the meniscus part not only by means of cutting methods but also by means of suitable shaping methods to bring the meniscus part directly into the proposed shape, for example by using plastics materials and carrying out thermoforming processes such as for example injection moulding, thermoforming, compression moulding or the like.

Preferably, the angle of aperture has a value in a range of ca. 20° to ca. 60°. Such an angular range ensures adequate guidance combined with the maximum surface contact of the parts of a knee-joint prosthesis that slide against one another. Advantageously, the angle of aperture has a value in a range of ca. 30° to ca. 50°.

Particularly good guidance of a femur part or a part thereof on the meniscus part may be achieved in particular if the longitudinal axes of the at least two trough-like recesses intersect in the region of the minimum of the width of the depression. Thus, a plurality of paths of motion in the region of the minimum of the width of the depression are practically delimited laterally or medially by a common boundary line or boundary point.

In order to form as homogeneous as possible a depression, in which a femur part or a part thereof may slide or roll in as trouble-free a manner as possible, it is advantageous if a depth of the at least two recesses relative to the upper side is identical or substantially identical.

For forming a depression that is oriented as symmetrically as possible, it is advantageous if one of the at least two trough-like recesses defines a longitudinal axis that extends in anterior-posterior direction.

For optimum lateral guidance in lateral and medial direction, it is advantageous if the depression in the region of the minimum of its width defines a direction that extends perpendicularly or substantially perpendicularly to the anterior-posterior direction. In particular, this allows a minimum spacing of lateral boundaries or edges of the depression to extend in lateral-medial direction.

In order as far as possible to avoid punctiform or linear loading of the meniscus part by the femur part or a part thereof, it is advantageous if the anterior end region and/or the posterior end region of the depression are rounded off in a direction away from the depression. In particular, the end regions may be rounded off in anterior and/or posterior direction. Thus, conventionally spherical or cylindrical surfaces of the femur parts may rest with the maximum surface on the meniscus part even in extreme positions between tibia and femur, i.e. in particular in states of maximum flexion or extension.

According to a preferred form of construction of the invention it may be provided that the posterior end region merges directly in a transition region between the upper side and a peripheral edge surface of the meniscus part. Such a development allows a particularly compact construction of the knee joint.

In order to prevent damage to tissue surrounding the meniscus part, in particular to tendons and ligaments, it is advantageous if edges of the meniscus part are rounded off in the transition region from the upper side to an at least partially peripheral lateral surface.

Preferably, a connection device is provided for connecting the meniscus part to a tibia part of a knee-joint prosthesis. This allows the meniscus part to be mounted in a defined manner on a tibia part.

In principle, it might be conceivable to form the connection device for the movable mounting of the meniscus part on the tibia part. For increased stability of the knee joint, it is however advantageous if the connection device is configured for immovable connection of the meniscus part to a tibia part.

The connection device may be of a particularly simple form if it comprises at least one first connection element, which is disposed on the meniscus part and which in a connection position is in engagement with at least one second connection element disposed on a tibia part. Such a connection device in particular makes it possible during a surgical procedure to connect an optimally matching meniscus part to an already implanted tibia part in order for example to adjust an optimum spacing between femur and tibia. This may be particularly important in order to place the tendons and ligaments connecting the tibia and the femur back under their natural tension.

The at least one connection element is advantageously configured in the form of a connection projection or in the form of a connection receiver. Connection elements formed in this way are particularly easy to manufacture and arrange in such a way that they are oriented transversely or substantially transversely of a load direction defined by a load introduced from the femur onto the meniscus part in order to prevent a detachment of the meniscus part from the tibia part.

To eliminate the need for tools to connect the meniscus part to the tibia part, it is advantageous if the at least one first connection element is configured in the form of a first detent element, which in the connection position is movable into engagement with the at least one second connection element configured in the form of a corresponding detent element. Detent elements may be configured in particular in the form of detent projections or detent recesses, which in the connection position are in engagement.

In order as far as possible to cover a large area of a partially resected tibia, it is advantageous if a posterior end of the meniscus part is rounded off.

Preferably, an anterior end of the meniscus part is configured in the form of a rounded-off tip. The rounded-off tip is oriented preferably in anterior direction. This allows the meniscus part to be optimally at least partially adapted to an external contour of a tibia part.

Advantageously, the meniscus part is manufactured from at least one biocompatible material. This prevents rejection reactions after implantation of the meniscus part.

It is advantageous if the at least one biocompatible material is a plastics material. Particularly suitable here is polyethylene. It is advantageous if the material is polyethylene of a high density and high molecular weight.

Particularly easy manufacture and a simple construction of the meniscus part may be achieved if it is configured symmetrically or substantially symmetrically relative to a mirror plane that extends in anterior-posterior direction. This development moreover has the advantage that the meniscus part may be configured in particular as a unicondylar meniscus part. This makes it possible to mount both medial and lateral femoral condyles in the same meniscus part. This reduces the manufacturing outlay and stockholding as only one meniscus part shape is needed for optional lateral or medial implantation of a unicondylar knee-joint prosthesis.

So that the meniscus part may be used to form a unicondylar knee-joint prosthesis, it is advantageous if the meniscus part has only a single femoral joint surface. Thus, in particular femoral joint surfaces may be individually adapted and implanted.

The present invention also relates to a meniscus part set for a knee-joint prosthesis comprising a tibia part and at least one meniscus part. The meniscus part is mounted immovably on the tibia part. The meniscus part set comprises two or more differently shaped meniscus parts, wherein at least one meniscus part of the set is one of the above described meniscus parts.

The meniscus part set then likewise presents the advantages described above in connection with the various forms of construction of the meniscus parts.

Moreover, the present invention relates to a knee-joint prosthesis having an artificial tibia part and having an artificial meniscus part. The artificial meniscus part is mounted movably or immovably on the tibia part and at an upper side has at least one femoral joint surface for the movable mounting of an artificial, natural or machine condyle of a femur. The at least one femoral joint surface is configured in the form of a depression facing away from the meniscus part. The depression has an anterior and a posterior end region and a width of the depression has a minimum between the anterior and the posterior end region.

Such a knee-joint prosthesis, as already explained initially in connection with the meniscus part according to the invention, has the advantage that a load introduction of loads from the femur onto the tibia may be optimized by virtue of a greater surface contact and/or lower transverse forces even in the case of a rotated tibia implant, for example as a result of incorrect implantation or a rotation of the tibia.

It is therefore further advantageous if the meniscus part is one of the meniscus parts described above. The advantages of the respective meniscus part have a likewise positive influence on the knee-joint prosthesis as a whole.

According to a preferred form of construction of the invention it may be provided that the knee-joint prosthesis comprises an artificial femur part and that the femoral joint surface comprises at least one femoral articular surface for the movable mounting of at least one artificial condyle or a condyle of the artificial femur part. By providing a femur part, a damaged knee joint may be replaced medially and/or laterally by an artificial knee-joint prosthesis.

It is advantageous if the tibia part has at least one anchoring element for anchoring in a tibia. In this way, a lasting stability of the knee-joint prosthesis after implantation may be ensured. Two, three or more anchoring elements may be provided. Projections protruding from the tibia part are in particular conceivable, for example in the form of fins extending in anterior-posterior direction.

It is advantageous if a connection device is provided for connecting the meniscus part to the tibia part. This in particular allows the meniscus part to be separated from the tibia part if for example it is worn and the tibia part has to be explanted. This moreover also allows individual combinations of tibia parts and meniscus parts to be selected even during a surgical procedure that is to be performed for implantation of the knee-joint prosthesis.

For increased stability of the knee-joint prosthesis, it is advantageous if the connection device is configured for the immovable connection of the meniscus part to the tibia part.

The construction of the connection device is particularly simplified if it comprises at least one first connection element, which is disposed on the meniscus part and which in a connection position is in engagement with at least one second connection element disposed on the tibia part.

Particularly simple and secure connections are achievable particularly if the at least one first or second connection element is configured in the form of a projection or in the form of a receiver. In particular, the receiver may be configured so as to correspond to the shape of the projection. Preferably, the projection positively fills the receiver in the connection position.

The meniscus part and the tibia part are easy to connect to one another if the at least one first connection element is configured in the form of a first detent element, which in the connection position is movable into engagement with the at least one second connection element configured in the form of a corresponding detent element. In particular, by providing such a detent connection it is possible entirely to dispense with a tool for connecting the meniscus part and the tibia part.

For increased stability of a connection between the meniscus part and the tibia part it is advantageous if the tibia part has a receiver, into which the meniscus part in a connection position at least partially positively or substantially positively engages. In particular, the receiver may be provided in addition to connection devices.

A connection between tibia part and meniscus part may be stabilized still further and in particular also secured if the at least one second connection element is disposed in or on the receiver.

Particularly good guidance may be achieved in particular if in a connection position the meniscus part is held immovably on the tibia part. This in particular also allows an increased stability of the knee-joint prosthesis as a whole.

Furthermore, the invention relates to a knee-joint prosthesis set having at least one tibia part, at least one femur part and at least one meniscus part that is mountable between the at least one tibia part and the at least one femur part movably or immovably on the at least one tibia part. The at least one meniscus part is one of the meniscus parts described above.

Such a knee-joint prosthesis set proves itself by virtue of the advantages already described above in connection with the various forms of construction of the meniscus part.

Figure 1:
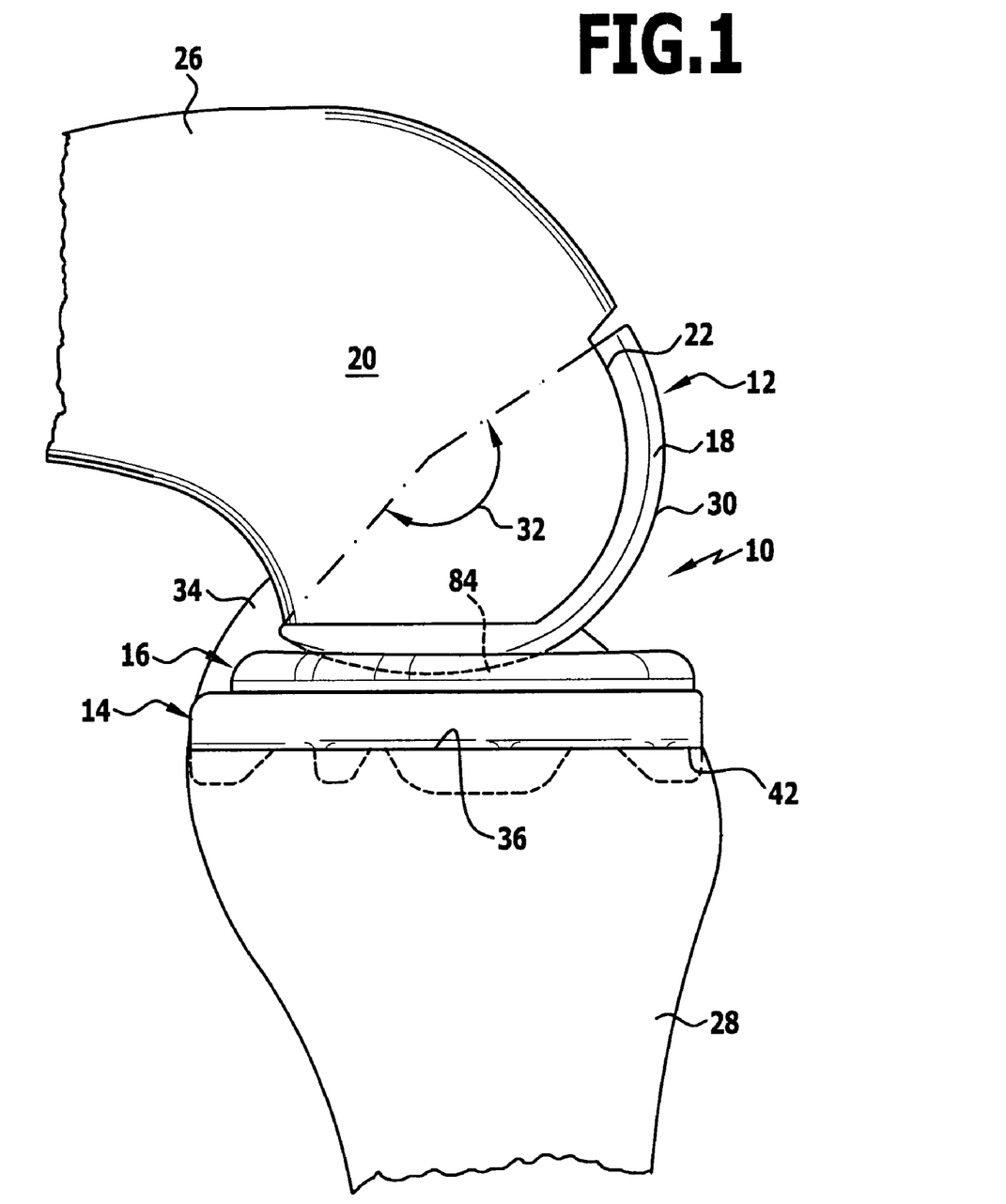
FIG. 1: a side view of an implanted unicondylar knee-joint prosthesis in flexion position of the knee joint.
Figure 2:
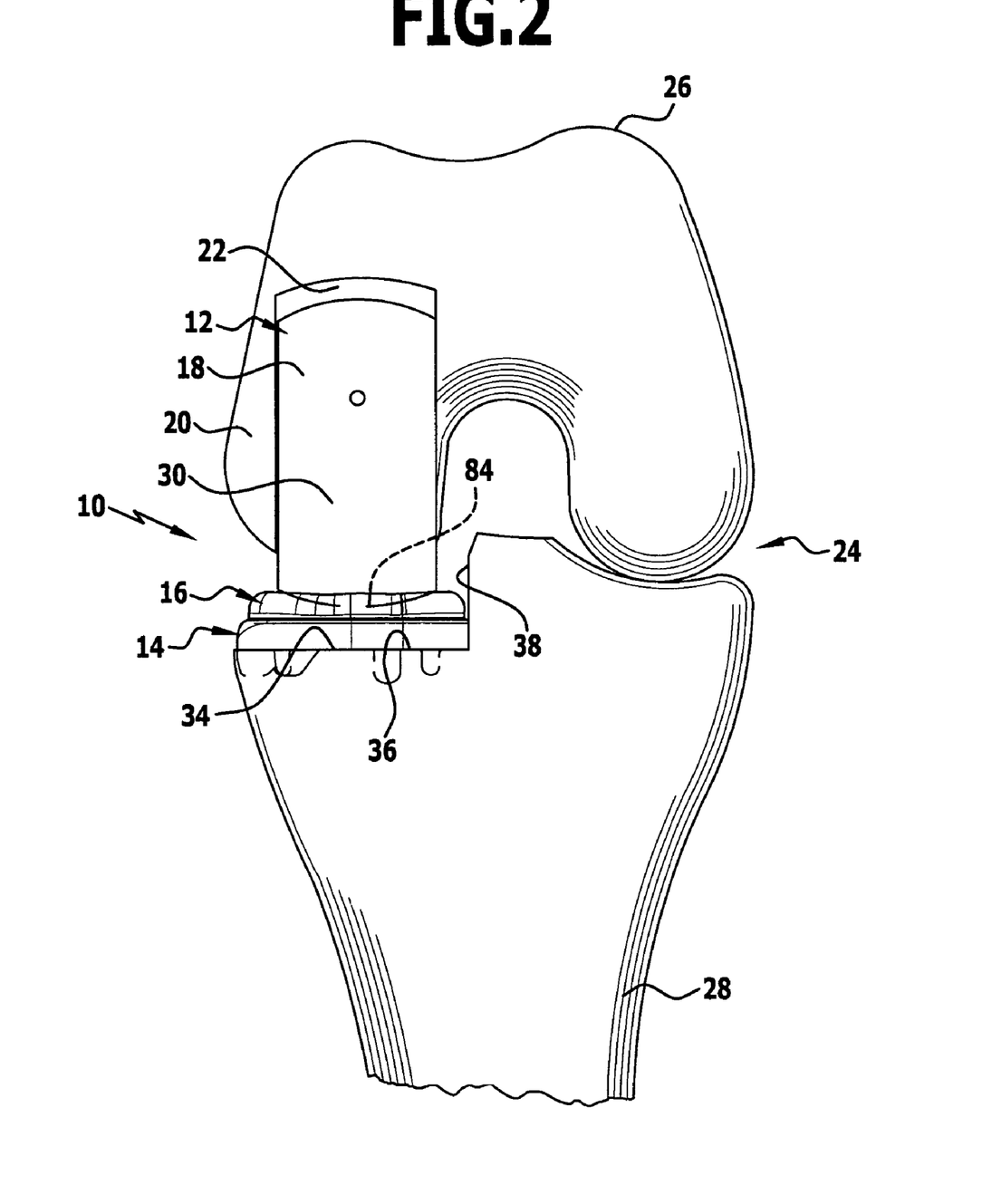
FIG. 2: a view of the knee joint of FIG. 1 from the front.

FIGS. 1 and 2 show by way of example an implanted knee-joint prosthesis provided as a whole with the reference character 10 and comprising a femur part 12, a tibia part 14 and, disposed between these, a meniscus part 16. The knee-joint prosthesis 10 is used for the partial replacement of a natural knee joint 24, which is formed between a distal end of a femur 26 and a proximal end of a tibia 28.

The femur part 12 is configured in the form of an artificial condyle 18, which has a width in lateral-medial direction that is slightly smaller than a width of a natural femoral condyle 20. The condyle 18 may in particular have a shape as described in DE 203 02 180 U1, which with its entire disclosure is hereby simultaneously introduced into the present description. The condyle 18 is mounted, for example by means of screws or by means of bone cement, for example on a recess 22 prepared for this purpose on the femoral condyle 20.

The condyle 18 defines an articular surface 30 facing away from the femur 26 and defining part of a spherical surface. It extends approximately over an angle at circumference 32 in a sagittal plane, wherein in every relative position of the femur 26 relative to the tibia 28, i.e. both in extension and—as represented in FIGS. 1 and 2—in flexion, at least part of the articular surface 30 is facing in the direction of the tibia 28.

For fastening the tibia part 14 on the tibia 28 opposite the condyle 18 a cutout 34 is incorporated into the tibia and defines a seating surface 36 that extends parallel or substantially parallel to a transverse plane. In lateral and/or medial direction, depending on whether the tibia part 14 is to be inserted laterally or medially, the cutout 34 is delimited at the remaining part of the tibia by a lateral surface 38 oriented perpendicularly to the seating surface 36.

Figure 6:
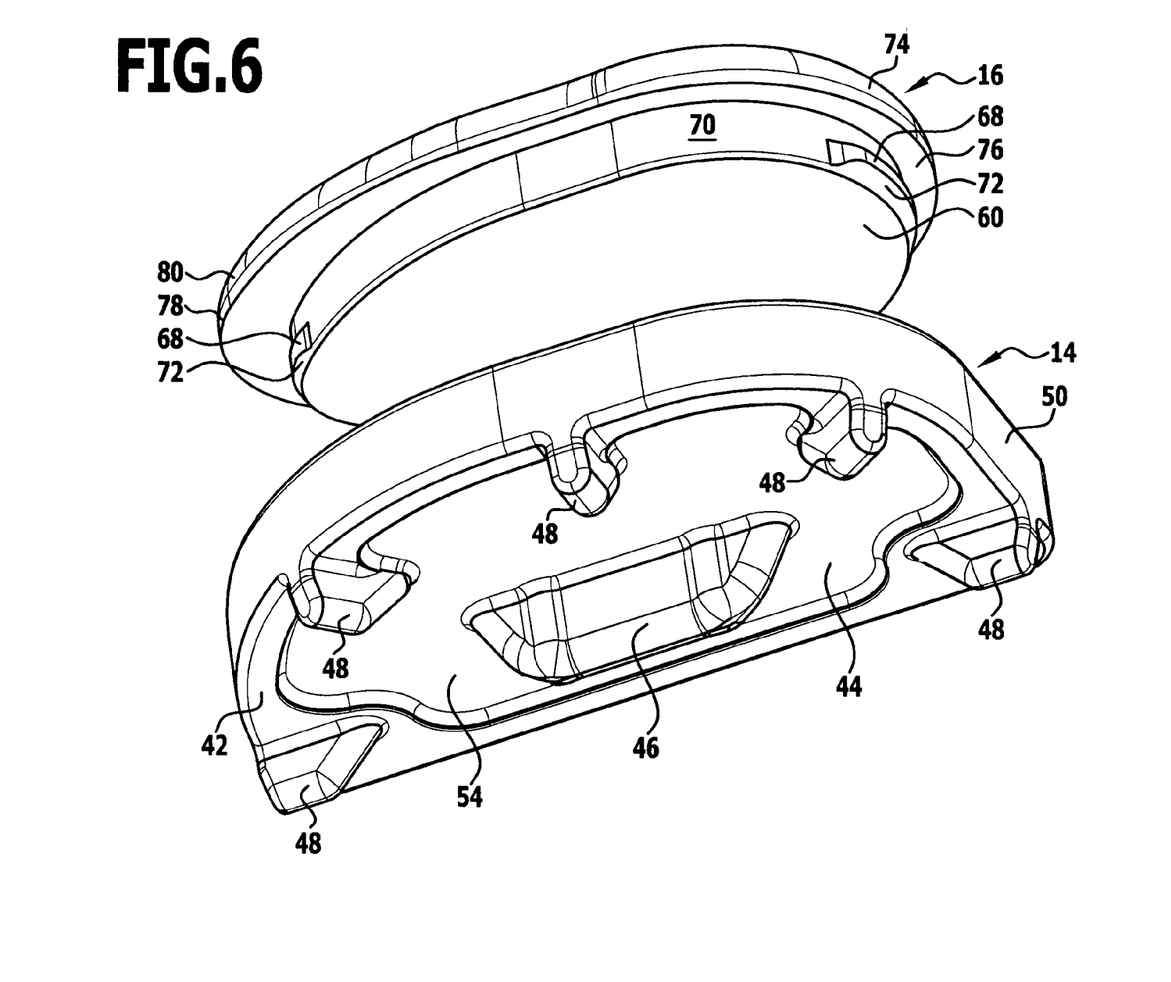
FIG. 6: an exploded view from below of the arrangement in FIG. 3.

The tibia part 14 is of a substantially cuboidal design and has a flat underside 40, which is delimited all the way round by a peripheral edge 42 that is formed so as to project vertically from the underside 40. Thus, as a whole a shallow recess 44 is defined, which is delimited by the edge 42 and the underside 40 and faces in the direction of the tibia 28. Disposed centrally in the middle of the underside 40 is a fin-like projection 46 that is aligned parallel to a sagittal plane. It extends approximately over a third of a length of the tibia part 14 in anterior-posterior direction.

Furthermore, for optimized anchoring of the tibia part 14 on the seating surface 36 further anchoring projections 48 are arranged distributed over the circumference of the edge 42 and terminate flush with a peripheral lateral surface 50 oriented perpendicularly to the underside 40. Disposed in an anterior and a posterior end region of the tibia part 14 there is in each case an anchoring projection 48 that is arranged parallel but laterally offset relative to the projection 46. A height of the anchoring projections 48 corresponds to an overall height of the projection 46, so that the regions of the anchoring projections 48 and of the projection 46 that project furthest from the tibia part 14 define a plane extending parallel to the underside 40.

In the region of the described anchoring projections 48 in the anterior and posterior end region of the tibia part 14 the edge 42 is widened. An anchoring projection 48 oriented transversely of the projection 46 projects, as do two anchoring projections 48 inclined at an angle of approximately 45° relative to the projection 46, slightly inwards from the edge 42 in the direction of the projection 46.

A lateral surface portion 52 of the lateral surface 50 extends parallel to the projection 46 and lies, after implantation of the tibia part 14 in the cutout 34, flat against the lateral surface 38. Otherwise, the tibia part 14 in plan view is formed substantially in the shape of a capital D, i.e. lateral surface portions of the lateral surface 50 disposed perpendicularly to one another merge into one another in a rounded-off manner. This prevents the tibia part 14 from projecting beyond a boundary of the seating surface 36 and ensures that the tibia part 14 covers this seating surface 36 as completely as possible.

Figure 3:
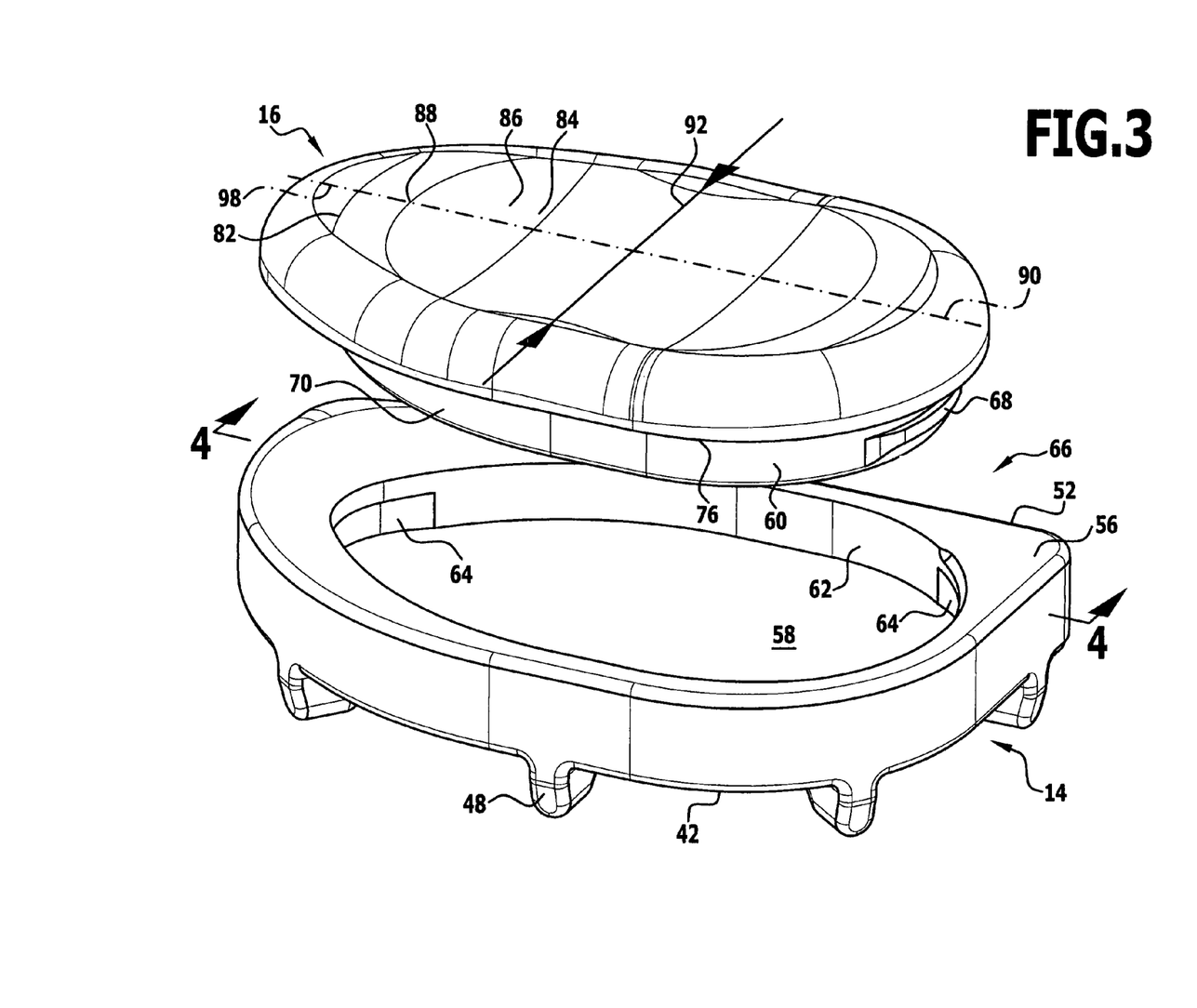
FIG. 3: an exploded view from above of the tibia part with meniscus part represented in FIGS. 1 and 2.

A base 54 of the tibia part 14 separates the recess 44 from a recess 58 facing away from an upper side 56 of the tibia part 14 and used to receive a positively-locking configured base portion 60 of the meniscus part 16. In plan view the recess 58, like the meniscus part 16 as a whole, is substantially in the shape of an egg having a rounded-off wide end, which faces in posterior direction, and a rounded-off tapered end, which faces in anterior direction. The recess 58 is laterally delimited by a peripheral, corner- and/or edge-free marginal surface 62 that is oriented perpendicularly to the upper side 56. Formed in the marginal surface 62 in the region of an anterior end of the recess 58 as well as in the region of a posterior end of the recess 58 are two undercut receivers 64, which in the sense of the claims define two connection elements of a connection device provided as a whole with the reference character 66 for connecting the tibia part 14 to the meniscus part 16. The receivers 64 extend in peripheral direction of the marginal surface 62 over an angular range of ca. 20° to 30° and are used to receive corresponding detent projections 68, which are disposed so as to be oriented away from a peripheral lateral surfaces 70 of the base portion 60. Lateral surfaces of the detent projections 68 facing in the direction of the base 54 are inclined slightly relative to a plane defined by the base 54, thereby forming oblique slide-on surfaces 72 that are oriented slightly in anterior and/or in posterior direction and facilitate a detent connection of the meniscus part 16 in the recess 58 of the tibia part 14. The meniscus part 16 may therefore be practically clipped into the tibia part 14.

Projecting beyond the lateral surface 70 is a rim-like flange 74 of the meniscus part 16 that defines a seating surface 76, which extends perpendicularly to the lateral surface 70 and which in a connection position, in which the meniscus part 16 is connected to the tibia part 14, rests on the upper side 56 of the tibia part 14. A peripheral lateral surface 78 of the meniscus part 16 is formed perpendicularly to the seating surface 76 but is rounded off in a transition region 80 to an upper side 82 of the meniscus part 16. A radius of the transition region 80 may correspond approximately to a thickness of the flange 74 perpendicularly to the seating surface 76.

Figure 4:
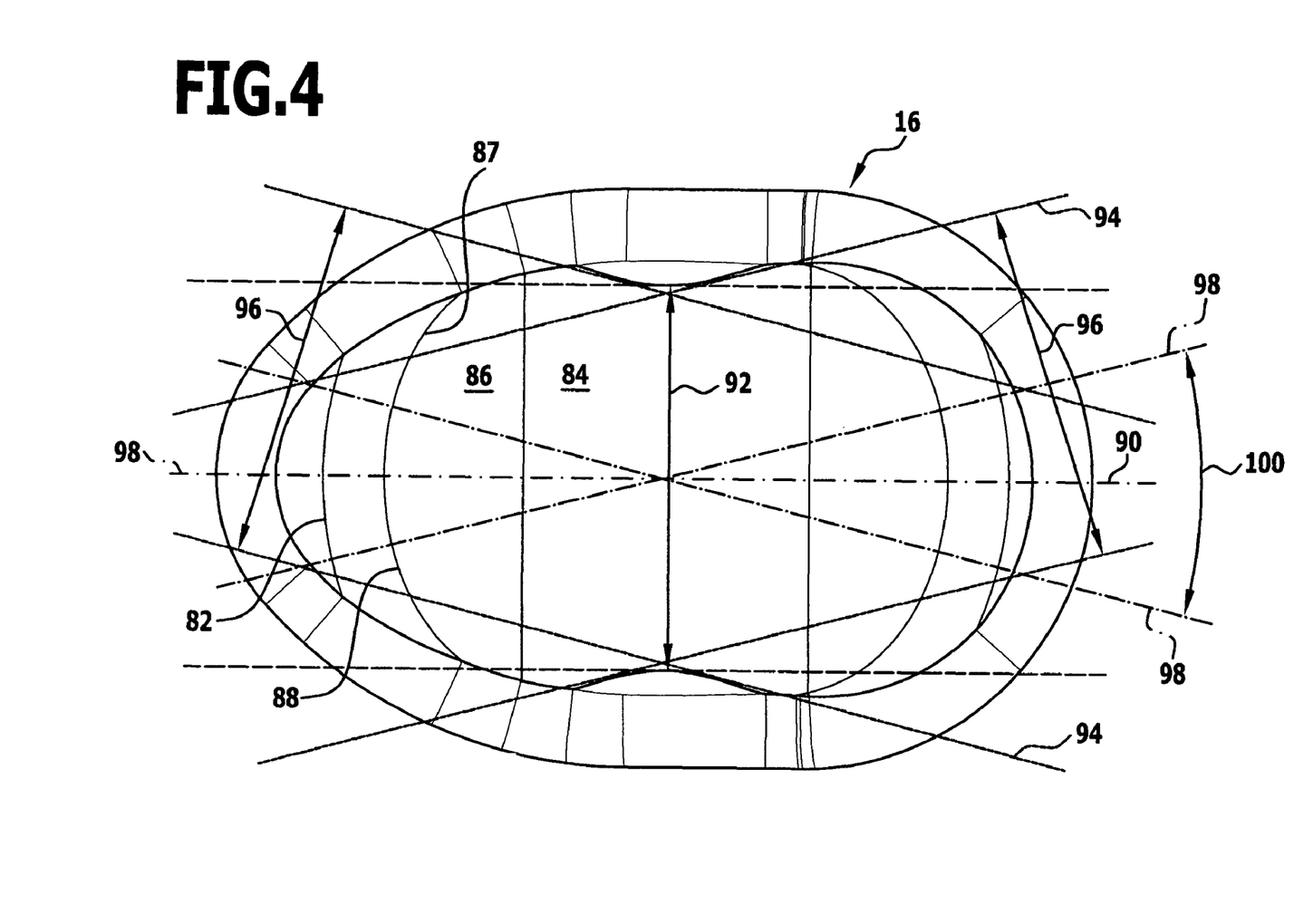
FIG. 4: a plan view from above of the meniscus part of FIG. 3.

In the upper side 82 a femoral joint surface 84 is formed for the movable mounting of the condyle 18. The femoral joint surface is configured in the form of a depression 86, which faces away from the meniscus part 16 and has an anterior end region 88 oriented in anterior direction and a posterior end region 90 oriented in posterior direction, wherein a width 92 of the depression 86 has a minimum between the anterior and the posterior end region 88, 90. Here, a minimum means that a width 92 of the depression 86 is minimal between the two end regions 88 and 90. The minimum of the width 92 may also be described as a constriction of the depression 86. The minimum of the width 92 may in particular be configured, as represented in FIG. 3, symmetrically between the two end regions 88 and 90. The anterior end region 88 and the posterior end region 90 of the depression 86 are rounded off or out in a direction away from said minimum, namely with a radius that corresponds to a radius of the articular surface 30. The result is, in plan view, a shape of the depression 86 that is lobe-like or butterfly-like. It may equally well be described as corresponding substantially to the external contour of a FIG. 8.

The shape of the depression 86 is formed in particular by a plurality of trough-like recesses 94, which in each case between the anterior and the posterior end region 88, 90 have a constant width 96 corresponding to the minimum of the width 92. The trough-like recesses 94, each of which has a concave inner surface of a design corresponding to the articular surface 30 in order to enable large-area seating thereof on the femoral joint surface 84, each define a longitudinal axis 98 that extends in a plane parallel or substantially parallel to the upper side 82. The longitudinal axes 98 of the trough-like recesses 94 most widely deflected in relation to a longitudinal axis 98 extending parallel to a sagittal plane define between them an angle of aperture 100. The angle of aperture 100 is an acute angle that preferably has a value in a range of ca. 20° to ca. 60°. The longitudinal axes 98 of the extreme recesses 94 intersect in the region of the minimum of the width 92 of the depression 86. A depth of the at least two recesses 94 in relation to the upper side 82 is identical or substantially identical. One of these recesses 94 defines a longitudinal axis 98 that extends in anterior-posterior direction. The depression 86 in the region of the minimum of its width 92, defined by the minimum spacing of a boundary of the depression 86, defines a direction that extends perpendicularly or substantially perpendicularly to the anterior-posterior direction.

Figure 5:
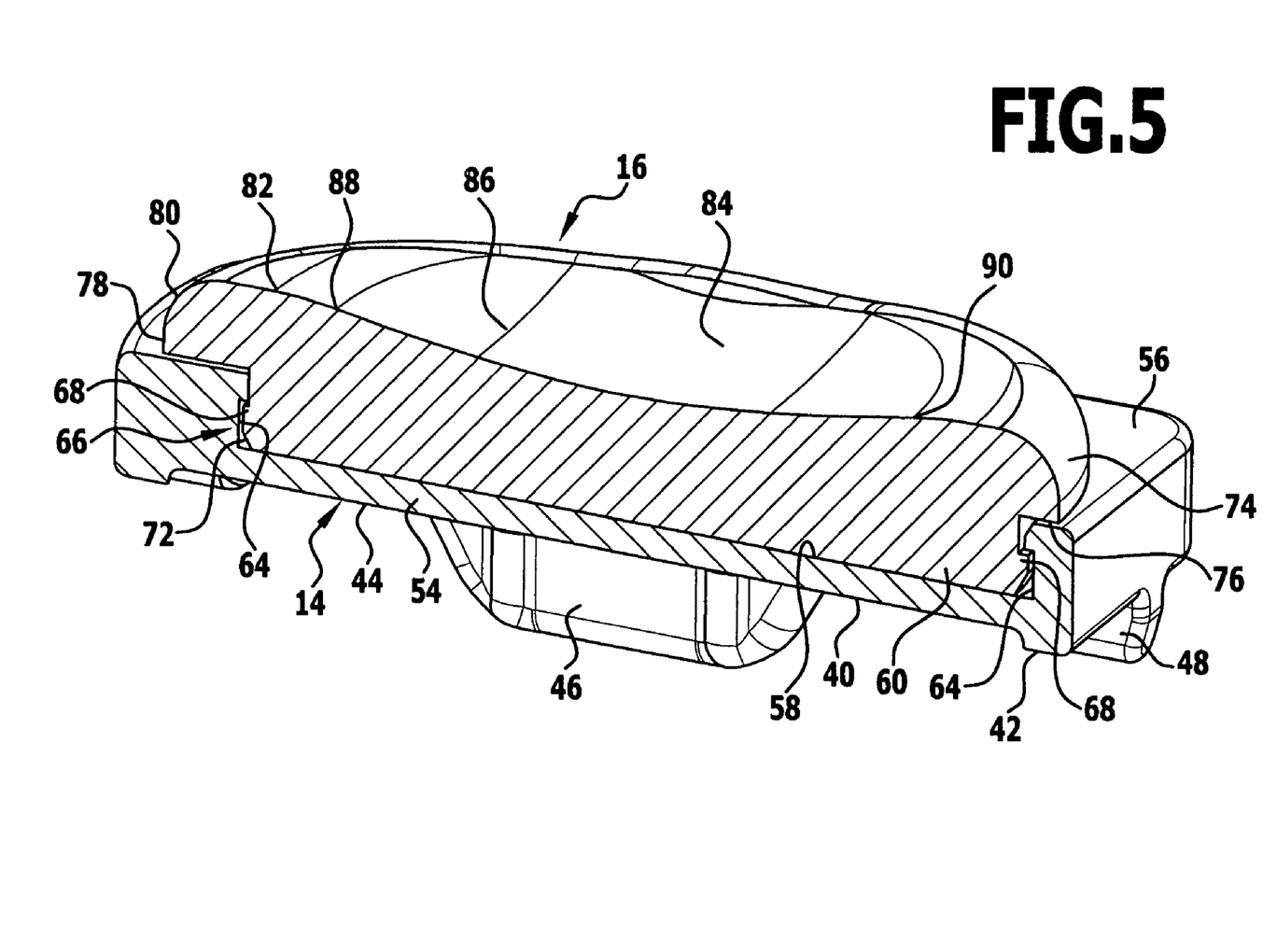
FIG. 5: a sectional view along line 4-4 in FIG. 3.

The meniscus part 16 is oriented as a whole mirror-symmetrically relative to a mirror plane, which contains the longitudinal axis 98 extending in anterior-posterior direction and which in FIG. 5 defines the sectional view. This allows the meniscus part 16 to be connected both to a medial tibia part 14, as represented in FIG. 2, and to a lateral tibia part 14, as represented in FIG. 3. The described meniscus part 16 is therefore usable both on the lateral side and on the medial side to form the unicondylar knee-joint prosthesis 10.

The special shaping of the depression 86 affords the condyle 18 the possibility of a large contact surface and low transverse forces even in the case of movements of the femur 26 that do not extend precisely in anterior-posterior direction. The symmetrical design of the meniscus part 16 makes it possible to halve the number of components of the knee-joint prosthesis 10 that have to be held in readiness during a surgical procedure. This means in particular that a knee-joint prosthesis set may be provided with a plurality of different meniscus parts 16 and/or tibia parts 14 and/or femur part 12 that may differ in shape, mutually corresponding radii of the articular surface 30, height of the flange 74 and other design parameters, in particular also in the angle of aperture 100. It is therefore possible, even during a surgical procedure to treat the partially damaged knee joint 24, for the surgeon to select the best fitting component in each case.

The described meniscus part 16 further allows a large-surface load introduction from the condyle 18 even taking into account a tibia 28 rotated in relation to a longitudinal axis of the femur 26, which may occur for example as a result of incorrect implantation or rotation owing to a movement of the bones relative to one another, seating of the articular surface 30 on the femoral joint surface 64 as well as arising transverse forces.

All of the parts of the knee-joint prosthesis 10 are manufactured preferably from biocompatible materials, wherein in the case of the meniscus part 16 this may be in particular a plastics material. In this case, it may be a polyethylene of a high density and high molecular weight.

Figure 7:
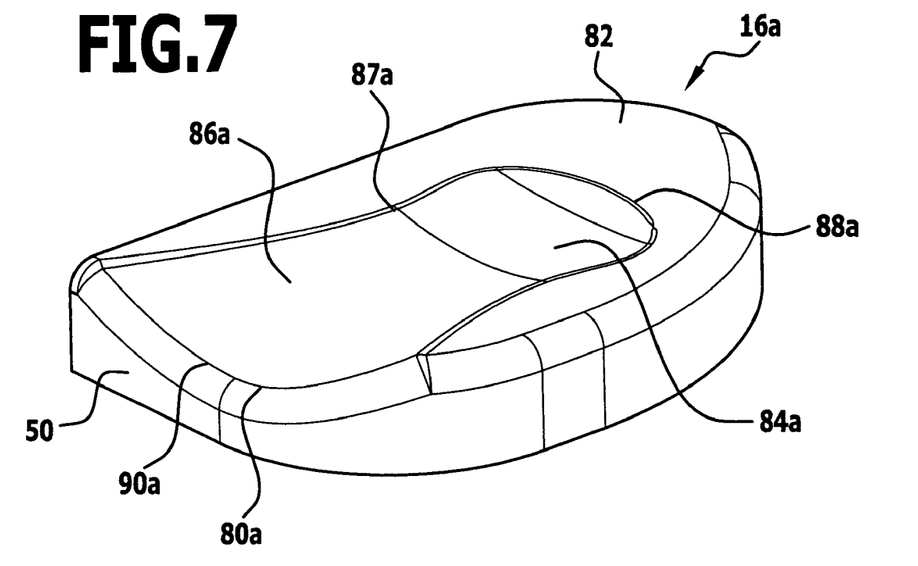
FIG. 7: a perspective view from above of a further embodiment of a meniscus part.
Figure 8:
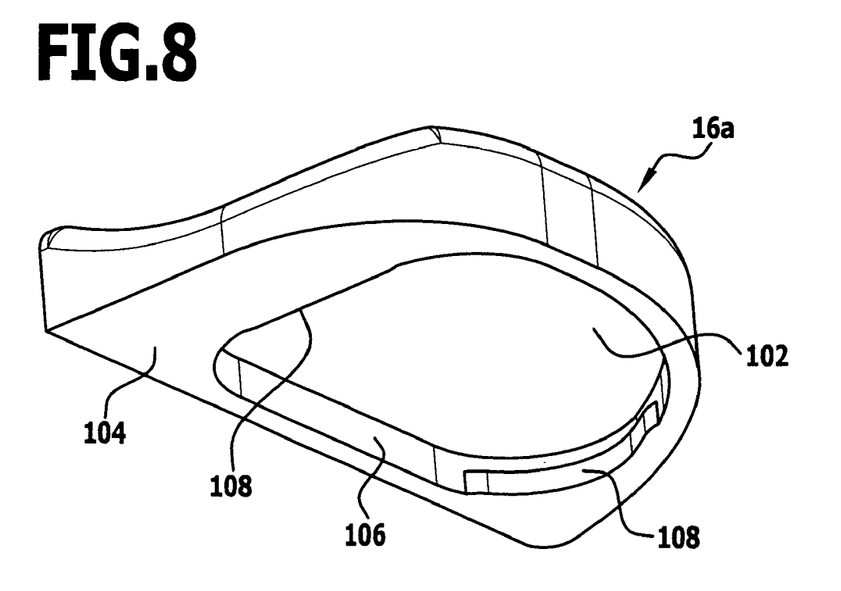
FIG. 8: a perspective view from below of the meniscus part of FIG. 7.

FIGS. 7 and 8 show a variant of the meniscus part that is provided as a whole with the reference character 16a. It differs from the meniscus part 16 in that a posterior end region 90a of the depression 86a merges, not into the upper side 82, but directly into the peripheral lateral surface 50. In the region of a posterior end of the meniscus part 16, therefore, the transition region 80a and the posterior end region 90a coincide or substantially coincide. A further result is that the posterior end region in plan view is delimited by an external contour of the meniscus part 18. All of the remaining features relating to a femoral joint surface 64a of the meniscus part 16a as well as a shape of the upper side 82 are identical to those of the meniscus part 16.

In contrast to the meniscus part 16, however, at a flat underside 104 a recess 102 is provided for forming a connection element that is to be brought into engagement with a connection element in the form of a projection that is formed on a non-illustrated tibia part. On a peripheral inner marginal surface 116 of the recess 102 that is oriented perpendicularly to the underside, further connection elements in the form of projections 108 oriented perpendicularly away from the marginal surface 116 and approximately parallel to the underside 104 are formed both in an anterior end region of the recess 102 and in a posterior end region of the recess 102 and in a similar manner to the detent projections 68 in a connection position, in which the meniscus part 16a is connected to a correspondingly configured tibia part, engage into corresponding detent recesses formed on a peripheral edge of a projection corresponding to the recess 102 and hence allow a simple clipping of the meniscus part 16a onto the tibia part.

The meniscus part 16a may be manufactured from the same materials as the meniscus part 16.

A meniscus part set is defined by two or more meniscus parts 16 and/or 16a, which may differ in their height and/or in the shape of the respective depressions 86 and/or 86a or other design parameters. A surgeon after implantation of the femur part 12 and the tibia part 14 may then select the most suitable meniscus part 16 and/or 16a for restoring optimum ligament and tendon tensions and clip it onto the tibia part.

The described knee-joint prostheses 10 are characterized by meniscus parts 16 and/or 16a that are fastenable immovably on the tibia part 14. Optionally, these meniscus parts may alternatively be mounted movably, for example displaceably or rotatably on the respective tibia part.

It is moreover also possible to use the described components to form a bicondylar knee-joint prosthesis. In this case, for example a femur part comprising two condyles would be selectable as well as a corresponding tibia part, wherein between the tibia part and the bicondylar femur part a one-piece meniscus part defining two femoral joint surfaces 84 and/or 84a is introduced. Such a meniscus part may be mounted both immovably or movably, for example displaceably and/or rotatably on an associated tibia part. Corresponding connection devices for connecting the meniscus parts to the associated tibia parts may be of an identical design to the connection devices 66 described above.

What is claimed is:

1. Artificial unicondylar meniscus part for a unicondylar knee-joint prosthesis, comprising:
a single femoral joint surface on an upper side of the meniscus part sized for the movable mounting of only a single artificial, natural or machined condyle of a femur, and
a depression formed in the femoral joint surface, said depression facing away from the meniscus part and having an anterior end region, a posterior end region and a width, said width having a minimum between the anterior end region and the posterior end region such that the depression in plan view defines a boundary line with the upper side that corresponds substantially to an external contour of a figure eight,
wherein the figure eight contour of the depression minimizes wear of the meniscus part by providing a large surface for contact with the condyle, and by reducing transverse forces acting upon the meniscus part during femoral movements that do not extend in an anterior-posterior direction relative to the meniscus part.

2. Meniscus part according to claim 1, wherein:
the depression is formed by at least two superimposed trough-like recesses, which in each case between the anterior end region and the posterior end region have a constant width, and which define longitudinal axes in a plane parallel or substantially parallel to the upper side, and
the longitudinal axes form between them an acute angle of aperture oriented in at least one of an anterior and a posterior direction.

3. Meniscus part according to claim 2, wherein the angle of aperture has a value in a range of about 20° to about 60°.

4. Meniscus part according to claim 2, wherein the longitudinal axes of the at least two trough-like recesses intersect in a region of the minimum of the width of the depression.

5. Meniscus part according to claim 2, wherein a depth of the at least two recesses in relation to the upper side is identical or substantially identical.

6. Meniscus part according to claim 2, wherein one of the at least two trough-like recesses defines a longitudinal axis that extends in the anterior-posterior direction.

7. Meniscus part according to claim 1, wherein the depression in a region of the minimum of the width defines a direction that extends perpendicularly or substantially perpendicularly to the anterior-posterior direction.

8. Meniscus part according to claim 1, wherein at least one of the anterior end region and the posterior end region of the depression are rounded off in a direction away from the depression.

9. Meniscus part according to claim 1, wherein the posterior end region merges directly into a transition region between the upper side and a peripheral marginal surface of the meniscus part.

10. Meniscus part according to claim 9, wherein edges of the meniscus part in the transition region from the upper side to an at least partially peripheral lateral surface are rounded off.

11. Meniscus part according to claim 1, wherein a connection device is provided for connecting the meniscus part to an artificial tibia part of an artificial knee-joint prosthesis.

12. Meniscus part according to claim 11, wherein the connection device is configured for an immovable connection of the meniscus part and the tibia part.

13. Meniscus part according to claim 11, wherein the connection device comprises at least one first connection element and at least one second connection element, said at least one first connection element is disposed on the tibia part, said at least one second connection element is disposed on the meniscus part, said at least one first connection element is in engagement with said at least one second connection element in a connection position.

14. Meniscus part according to claim 13, wherein the at least one first connection element is configured in the form of a connection projection or in the form of a connection receiver.

15. Meniscus part according to claim 13, wherein the at least one first connection element is configured in the form of a first detent element that in the connection position is movable into engagement with the at least one second connection element configured in the form of a corresponding detent element.

16. Meniscus part according to claim 1, wherein a posterior end of the meniscus part is rounded off.

17. Meniscus part according to claim 1, wherein an anterior end of the meniscus part is configured in the form of a rounded-off tip.

18. Meniscus part according to claim 1, wherein the meniscus part is manufactured from at least one biocompatible material.

19. Meniscus part according to claim 18, wherein the at least one biocompatible material is a plastic material.

20. Meniscus part according to claim 1, wherein the meniscus part is configured symmetrically or substantially symmetrically relative to a mirror plane that extends in the anterior-posterior direction.

21. Artificial unicondylar meniscus part set for a unicondylar knee-joint prosthesis comprising an artificial tibia part and at least one artificial unicondylar meniscus part, wherein the at least one meniscus part is mounted immovably on the tibia part, the meniscus part set comprising:
two or more differently shaped artificial unicondylar meniscus parts,
wherein at least one of the two or more meniscus parts of the set is an artificial meniscus part which comprises:
a single femoral joint surface on an upper side of the meniscus part sized for the movable mounting of only a single artificial, natural or machined condyle of a femur, and
a depression formed in the femoral joint surface, said depression facing away from the meniscus part and having an anterior end region, a posterior end region and a width, said width having a minimum between the anterior end region and the posterior end region such that the depression in plan view defines a boundary line with the upper side that corresponds substantially to an external contour of a figure eight,
wherein the figure eight contour of the depression minimizes wear of the meniscus part by providing a large surface for contact with the condyle, and by reducing transverse forces acting upon the meniscus part during femoral movements that do not extend in an anterior-posterior direction relative to the meniscus part.

22. Artificial knee-joint prosthesis comprising:
an artificial tibia part, and
an artificial unicondylar meniscus part, said meniscus part is mountable movably or immovably on the tibia part and comprises:

a single femoral joint surface on an upper side of the meniscus part sized for the movable mounting of only a single artificial, natural or machined condyle of a femur, and a depression formed in the femoral joint surface, said depression facing away from the meniscus part and having an anterior end region, a posterior end region and a width, said width having a minimum between the anterior end region and the posterior end region such that the depression in plan view defines a boundary line with the upper side that corresponds substantially to an external contour of a figure eight, wherein the figure eight contour of the depression minimizes wear of the meniscus part by providing a large surface for contact with the condyle, and by reducing transverse forces acting upon the meniscus part during femoral movements that do not extend in an anterior-posterior direction relative to the meniscus part.

23. Knee-joint prosthesis according to claim 22, wherein:
the depression is formed by at least two superimposed trough-like recesses, which in each case between the anterior end region and the posterior end region have a constant width, and which define longitudinal axes in a plane parallel or substantially parallel to the upper side and the longitudinal axes form between them an acute angle of aperture oriented in at least one of anterior and posterior direction.

24. Knee-joint prosthesis according to claim 22, wherein the knee-joint prosthesis comprises an artificial femur part and the femoral joint surface comprises a femoral articular surface for the movable mounting of a condyle of the artificial femur part.

25. Knee-joint prosthesis according to claim 22, wherein the tibia part has at least one anchoring element for anchoring in a tibia.

26. Knee-joint prosthesis according to claim 22, wherein a connection device is provided for connecting the meniscus part to the tibia part.

27. Knee-joint prosthesis according to claim 26, wherein the connection device is configured for an immovable connection of the meniscus part to the tibia part.

28. Knee-joint prosthesis according to claim 26, wherein the connection device comprises at least one first connection element and at least one second connection element, said at least one first connection element is disposed on the tibia part, said at least one second connection element is disposed on the meniscus part, said at least one first connection element is in engagement with said at least one second connection element in a connection position.

29. Knee joint prosthesis according to claim 28, wherein the at least one first or second connection element is configured in the form of a projection or in the form of a receiver.

30. Knee-joint prosthesis according to claim 28, wherein the at least one first connection element is configured in the form of a first detent element, which in the connection position is movable into engagement with the at least one second connection element configured in the form of a corresponding detent element.

31. Knee-joint prosthesis according to claim 28, wherein the tibia part has a receiver, into which in a connection position the meniscus part at least partially positively or substantially positively engages.

32. Knee-joint prosthesis according to claim 31, wherein the at least one second connection element is disposed in or on the receiver.

33. Knee-joint prosthesis according to claim 22, wherein in a connection position the meniscus part is held immovably on the tibia part.

34. Artificial knee-joint prosthesis set comprising:
at least one artificial tibia part, at least one artificial femur part, and at least one artificial unicondylar meniscus part, said at least one meniscus part mountable between the at least one tibia part and the at least one femur part movably or immovably on the at least one tibia part, one of the at least one meniscus parts comprising:

a single femoral joint surface on an upper side of the meniscus part sized for the movable mounting of only a single artificial condyle of a femur, and a depression formed in the femoral joint surface, said depression facing away from the meniscus part, and having an anterior end region, a posterior end region and a width, said width having a minimum between the anterior end region and the posterior end region such that the depression in plan view defines a boundary line with the upper side that corresponds substantially to an external contour of a figure eight, wherein the figure eight contour of the depression minimizes wear of the meniscus part by providing a large surface for contact with the condyle, and by reducing transverse forces acting upon the meniscus part during femoral movements that do not extend in an anterior-posterior direction relative to the meniscus part.

* * * * *